(12) United States Patent
Swanbom

(10) Patent No.: US 7,223,238 B2
(45) Date of Patent: May 29, 2007

(54) METHOD AND DEVICE FOR MARKING SKIN DURING AN ULTRASOUND EXAMINATION

(76) Inventor: Rebecca L. Swanbom, 1125 4050 Rd., Paonia, CO (US) 81428

( * ) Notice: Subject to any disclaimer, the term of this patent is extended or adjusted under 35 U.S.C. 154(b) by 242 days.

(21) Appl. No.: 10/968,563

(22) Filed: Oct. 18, 2004

(65) Prior Publication Data

US 2005/0085727 A1 Apr. 21, 2005

Related U.S. Application Data

(63) Continuation-in-part of application No. 10/057,272, filed on Jan. 24, 2002, now Pat. No. 6,805,669.

(60) Provisional application No. 60/264,359, filed on Jan. 25, 2001.

(51) Int. Cl.
*A61B 8/00* (2006.01)
(52) U.S. Cl. .................................. 600/437; 600/459
(58) Field of Classification Search ................ 600/437, 600/443, 459; 33/18.1, 32.1, 41.1, 0.4, 0.6, 33/262, 574
See application file for complete search history.

(56) References Cited

U.S. PATENT DOCUMENTS

| | | | |
|---|---|---|---|
| 3,502,070 A | 3/1970 | Bliss | 128/2 |
| 3,628,717 A * | 12/1971 | Lynch et al. | 228/6.2 |
| 3,810,459 A | 5/1974 | Becker | 600/453 |
| 4,030,414 A | 6/1977 | McGuire | 101/379 |
| 4,092,980 A | 6/1978 | Frank et al. | 128/2 A |
| 4,127,842 A | 11/1978 | Hassler | 340/3 D |
| 4,183,353 A | 1/1980 | Gallub | 128/654 |
| 4,228,796 A | 10/1980 | Gardiner | 128/215 |
| 4,252,125 A | 2/1981 | Iinuma | 128/660 |
| 4,282,880 A | 8/1981 | Gardineer et al. | 128/660 |
| 4,362,157 A | 12/1982 | Keeth | 128/215 |
| 4,408,611 A | 10/1983 | Enjoji | 128/660 |
| 4,431,006 A | 2/1984 | Trimmer et al. | 600/461 |
| 4,466,443 A | 8/1984 | Utsugi | 128/660 |
| 4,535,781 A | 8/1985 | Hetz | 128/660 |
| 4,567,898 A | 2/1986 | Plugge et al. | 128/660 |
| 4,593,699 A | 6/1986 | Poncy et al. | 128/660 |
| 4,665,925 A | 5/1987 | Millar | 128/663 |
| 4,674,517 A | 6/1987 | Barnes et al. | 128/663 |
| 4,697,595 A | 10/1987 | Breyer et al. | 128/660 |
| 4,742,829 A | 5/1988 | Law et al. | 128/660 |
| 4,790,321 A | 12/1988 | Miwa et al. | 128/660.07 |
| 4,794,931 A | 1/1989 | Yock | 128/660.03 |
| 4,833,059 A | 5/1989 | Tomura et al. | 430/120 |
| 4,844,080 A | 7/1989 | Frass et al. | 128/660.01 |

(Continued)

Primary Examiner—Francis J. Jaworski
(74) Attorney, Agent, or Firm—Sheridan Ross PC

(57) ABSTRACT

A method and device for marking a patient's skin during an ultrasound examination to denote a feature of interest. The device comprises a first portion and a second portion. The first portion is adapted for attachment of the device to an ultrasound transducer. The second portion is adapted for marking the skin of the patient to denote the feature of interest. The first and second portions are rotatably attached to each other. During an ultrasound examination of the patient to locate the feature of interest, the second portion is rotated so that it is spaced away from the patient's skin. The ultrasound examination is conducted in the normal manner until the feature of interest is located, at which time the second portion is rotated so that it contacts and marks the patient's skin to denote the feature of interest.

3 Claims, 3 Drawing Sheets

U.S. PATENT DOCUMENTS

| | | | |
|---|---|---|---|
| 4,877,033 A | 10/1989 | Seitz, Jr. | 128/660.05 |
| 5,076,279 A | 12/1991 | Arenson et al. | 128/662.05 |
| 5,131,397 A | 7/1992 | Crowley | 600/463 |
| 5,152,293 A | 10/1992 | Vonesh et al. | 128/662.03 |
| 5,226,419 A | 7/1993 | Hanrahan et al. | 600/437 |
| 5,284,147 A | 2/1994 | Hanaoka et al. | 128/662.06 |
| 5,349,958 A | 9/1994 | Hanrahan et al. | 600/437 |
| 5,381,795 A | 1/1995 | Nordgren et al. | 128/663.01 |
| 5,469,852 A * | 11/1995 | Nakamura et al. | 600/463 |
| 5,485,845 A * | 1/1996 | Verdonk et al. | 600/463 |
| 5,596,990 A * | 1/1997 | Yock et al. | 600/467 |
| 5,671,747 A | 9/1997 | Connor | 128/662.06 |
| 5,792,059 A | 8/1998 | Furia et al. | 600/459 |
| 5,820,552 A | 10/1998 | Crosby et al. | 600/407 |
| 5,851,180 A | 12/1998 | Crosby et al. | 600/407 |
| 5,873,827 A | 2/1999 | Russell | 600/437 |
| 5,921,930 A | 7/1999 | Uberle | 600/439 |
| 6,292,180 B1 | 9/2001 | Lee | 345/177 |
| 6,325,769 B1 | 12/2001 | Klopetek | 601/2 |
| 6,361,499 B1 | 3/2002 | Bates et al. | 600/461 |
| 6,373,003 B1 | 4/2002 | Holtzman | 178/19.01 |
| 6,379,307 B1 | 4/2002 | Filly et al. | 600/461 |
| 6,405,072 B1 | 6/2002 | Cosman | 600/426 |
| 6,805,669 B2 * | 10/2004 | Swanbom | 600/437 |

* cited by examiner

METHOD AND DEVICE FOR MARKING SKIN DURING AN ULTRASOUND EXAMINATION

RELATED APPLICATION

The present invention is a continuation-in-part of U.S. patent application Ser. No. 10/057,272 filed on Jan. 24, 2002, now issued U.S. Pat. No. 6,805,669, which claims priority from U.S. Provisional Patent Application No. 60/264,359 filed in Jan. 25, 2001. The entire disclosure of the prior applications are considered to be part of the disclosure of the accompanying application and are hereby incorporated by reference.

FIELD OF THE INVENTION

The invention relates to a method and diagnostic ultrasound accessory for marking a patient's skin during an ultrasound examination.

BACKGROUND OF THE INVENTION

Never before has the diagnostic ultrasound examination been such an integral part of a physician's arsenal. With the expanding technology of medical imaging modalities and medical interventions, the global trend is towards less invasive medical procedures. Therefore, even more emphasis and value have been placed on the precision of pre-interventional diagnostic imaging modalities, including ultrasound.

Historically, a common application of ultrasound has been an ultrasound evaluation of a patient's greater saphenous vein prior to its use as a conduit for arterial surgical reconstruction for lower extremity revascularization in order to salvage a patient's ischemic leg. The ultrasound evaluation is done to save operation time, so the surgeon can avoid making an unnecessarily long incision down the entire length of the patient's leg, which often has non-healing wounds or gangrene present, and so the surgeon can avoid making an incision in the patient's leg only to discover that the desired vein is in a different location, is absent, is duplicated, or is not suitable for use. To determine whether a vein will be suitable, its patency, transverse diameter, quality and location are evaluated by an ultrasound technologist. If the vein is adequate, its course is marked on the patient's skin with a permanent marking pen.

The following procedure is one currently used to preform the ultrasound evaluation and marking of a patient's greater saphenous vein. A diagnostic ultrasound machine, ordinarily with a 7–10 MHZ linear array transducer, is used. The ultrasound technologist visually estimates the center of the face of the transducer and denotes it with a permanent marking pen line directly on the transducer housing. Another technique is to apply a transducer cover to protect the transducer housing and to mark the cover. The medial aspect of the patient's leg is prepped with alcohol to remove gel residues, lotions or oils. Ultrasound gel is applied, and the leg is scanned to track and mark the vein site, generally at two centimeter increments. The technologist visually centers the vein in the middle of the ultrasound screen, which should appear to correspond with the center of the transducer. The technologist slightly tilts the transducer and wipes the gel from the patient's skin beneath the transducer, with a cloth, while maintaining the transducer contact and, hence, position on the skin. The patient is asked to remove the cap from a permanent marking pen and to place it in the technologist's hand. The technologist marks a dot at the approximate site on the skin based on his/her visual estimation of the center of the transducer. The lights in the room are usually turned off throughout the ultrasound examination. Time is allowed for the ink to dry. Ultrasound gel is reapplied, and the area is re-scanned to confirm that the mark corresponds with the target vessel. Frequently, an error in marking is made, and an alcohol swab is used to erase the mark and the marking process is repeated. This tedious and cumbersome procedure is repeated over the entire length of at least one of the patient's legs. Often it is necessary to assess all four of the patient's extremities to find enough vein for a long composite vein bypass graft. Upon completion of the evaluation and marking, the room is re-lit, gel residue is removed, and the dot marks are lightly swabbed with alcohol to remove any residual gel. Generally, a new marker is now used to re-mark the skin and connect the dots. The patient is instructed not to wash off the marks, and the patient may need to re-mark them at home if the surgery is not scheduled for a few days. If a second technologist is available, one technologist will operate the ultrasound transducer and ultrasound machine controls, while the other technologist wipes away the gel and marks the skin.

Obviously, this method of marking the skin is inherently inaccurate, laborious, and unsophisticated for ultrasound technologists, physicians and other ultrasound operators. Numerous other ultrasound-guided skin-marking procedures are also in use, and all of them are equally deficient as the one just described. While ultrasound methods for identifying targets prior to physician intervention are becoming more valuable, with numerous applications, accuracy is lost because of the crude and cumbersome techniques employed for marking the skin above a feature of interest.

SUMMARY OF THE INVENTION

Accordingly, one of the objects of the present invention is to increase the accuracy and efficiency of ultrasound-guided skin-marking procedures.

Another object of the present invention is to enable an ultrasound operator to more easily produce a more accurate mark on a patient's skin above a feature of interest.

Yet another object of the present invention is to enable an ultrasound operator to produce a mark on a patient's skin above a feature of interest in a more technologically precise and sophisticated manner.

It is a further object of the present invention to provide a method for marking skin above a feature of interest during an ultrasound evaluation which is more accurate and efficient than current procedures.

It is another object of the present invention to provide a preferably disposable diagnostic ultrasound accessory for marking skin above a feature of interest that makes ultrasound-guided skin-marking procedures more accurate and efficient than current procedures.

It is a further object of the present invention to provide a preferably disposable diagnostic ultrasound accessory for marking skin above a feature of interest that is easily operated during use.

It is a particular object of this invention to provide a simple, yet highly accurate, easily-manipulated, preferably disposable diagnostic ultrasound accessory which an ultrasound technologist or operator can readily attach to an ultrasound transducer.

It is also a particular object of this invention to provide a simple, yet highly accurate, easily-manipulated, preferably disposable diagnostic ultrasound accessory, the overall geometry of which is designed for optimal ergonomics, accuracy and efficiency.

To attain the above-mentioned objects, the invention provides a method and device for marking a patient's skin during an ultrasound examination to denote a feature of interest. In one embodiment, the device comprises a first portion (or element) and a second portion. The first portion is adapted for attachment of the device to an ultrasound transducer. The second portion is adapted for marking the skin of the patient to denote the feature of interest. The first and second portions are rotatably attached to each other. During an ultrasound examination of the patient to locate the feature of interest, the second portion is moved, preferably rotated, so that it is spaced away from the patient's skin. The ultrasound examination is conducted in the normal manner until the feature of interest is located, at which time the second portion is moved, preferably rotated, so that it contacts and marks the patient's skin to denote the feature of interest. The gel need not be removed from the patient's skin to mark it, and the examination can be immediately resumed once the feature of interest is marked on the patient's skin and the second portion is moved, (e.g., rotated) again so that it is spaced away from the patient's skin. These procedures can be repeated as many times as needed to identify and mark all features of interest or to map a feature of interest (e.g., a vein). The entire ultrasound examination and accurate marking of all features of interest on the patient's skin can be performed by a single person in substantially less time than is required by current procedures.

Therefore, one embodiment of the present invention is directed to an ultrasound accessory for marking a patient's skin which comprises a first element adapted to be attached to an ultrasound transducer, a second element adapted for rotation with respect to the first element, such second element contacting a surface subject to ultrasound examination, and a marking element capable of marking a patient's skin attached to the second element. Preferably, the first and second element are movable with respect to each other, preferably in a rotatable fashion. In a still further preferred embodiment, a means for aligning the ultrasound accessory to ensure that the mark on a patient's skin corresponds to the image produced by the transducer, preferably being centered on an ultrasound image produced by the transducer and/or being centered by the ultrasound operator. The first element can be removably attached to the ultrasound transducer by any suitable means, including adhesive stickers, velcro, snaps or slide connectors, etc.

In other embodiments, the present invention is directed to an ultrasound accessory for marking a patient's skin utilizing a marking element that is attached to a body element adapted to be attached to an ultrasound transducer, such marking element capable of being brought into contact with a patient's skin in a manner that presents a visual or palpable indication of position. As one of skill in the art will also appreciate, a portion of the marking element could also be incorporated into the hinge or first element, such as by being retractable.

The present invention is further directed to a method of marking a patient's skin at a feature of interest during an ultrasound examination comprising the location of a feature of interest by conducting an ultrasound examination using a device that has a first element (a portion of the marking element could be incorporated/retracted into the hinge or first element) rotatably attached to a second element, a marking element capable of marking a patient's skin attached to the second element, and such first element being adapted for attachment to an ultrasound transducer; rotating the second element of the ultrasound accessory to contact a patient's skin with the marking element, and marking the patient's skin to denote a feature of interest, such marking preferably being performed in a manner that presents a visual and/or palpable indication of position.

The present invention is further directed to a device having a single portion/marking leaf (as opposed to two portions/marking leaves) that can be attached or otherwise associated or applied to a transducer, thus eliminating any need for a second leaf to serve as an attachment mechanism. In a preferred embodiment, such device is shaped like a cap that fits over the face of a transducer and preferably remains in place for the duration of an ultrasound exam, as opposed to alternative devices that can be rotated frequently during an exam to alternative positions.

It will therefore be appreciated that the present invention is directed to a method and an ultrasound device for indicating on a patient's skin a feature of interest, comprising a first element operatively associated with an ultrasound transducer and a second element movably associated with said first element, said second element having a marking element adapted for marking a patient's skin prior to or during an ultrasound examination. A further means for aligning the ultrasound device to assure that markings made on the patient's skin correspond to the ultrasound image produced by the transducer can be utilized. For example, a ruler sticker can be attached to either the first element or the second element, and can be used for aligning the device upon attachment to the transducer so that when the device is moved (e.g., rotated) into a proper place, the operator can be assured that the device is centered on the transducer.

In one embodiment an ultrasound image is created whereby the technologist is able to achieve a full field of view of the area of study. Such a field of view may be analyzed through stationary and/or dynamic ultrasound images. Prior to construction of such an image, the technologist may wish to narrow his or her field of view to isolate an area for study. In order to isolate an area, the technologist can move the transducer across the general area of study. In this process, the technologist will alternate his or her focus on the skin and the ultrasound imaging monitor/display until the given area appears in the correct field.

Aside from skin surface visual markers and/or anatomical landmarks, an ultrasound technologist has little guidance on where an ultrasound transducer is being applied. Even with the use of skin surface markers the technologist may have to move the transducer several times across a given area to determine an exact location. In accordance with one aspect of the present invention, the use of a reticle within the ultrasound image field helps guide the technologist's field of view with alternating focus. With the use of such a reticle, the technologist is able to more quickly and precisely line up the correct target zone for analysis.

The present invention provides for a method and device for guiding the ultrasound transducer during an ultrasound examination. In one embodiment of the present invention, the ultrasound technologist's examination movements are guided by a substantially vertical reticle appearing on the ultrasound imaging monitor/display. The vertical reticle is created by the interference of ultrasound waves produced by the acoustic interface of the ultrasound transducer. Materials that generally absorb, diverge, scatter or reflect ultrasound waves can be used to create the vertical reticle. Such materials can be imbedded in the transducer and/or can be attached as an accessory (e.g., including a cap that fits over the face of the transducer), to create an image of a vertical reticle. As ultrasound waves are produced, the interference material diverts a portion of ultrasound waves resulting in a negative image that appears on the ultrasound image monitor as a reticle. The technologist may then use the reticle (like crosshairs or any other suitable type of targeting device image) to identify the location of the area of study.

In one embodiment of the invention, the interference material can be comprised of various combinations of shape, density, wall thickness, and wall rigidity to provide for the desired shape and emphasis of the reticle produced. In a preferred embodiment, interference material is used to create two substantially vertical reticles at a set or predetermined distance. The two vertical reticles allow for the delineation of left and right (or in alternatively and/or in combination, top and bottom) margins and/or borders. The reticles may be used to align the area of study for further examination or imaging. In another embodiment of the invention, the distance between the reticles may be calibrated to a fixed distance. Once calibrated, the technologist may use the reticles to determine the approximate linear size of an area of study or legion.

This summary of the invention is not intended to fully describe each and every potentially important aspect of the present invention. One of skill in the art will understand from the entire specification, including the drawings, claims, detailed description, etc., the full scope of the present invention.

Another embodiment of this invention is directed to an electronic method, which produces a vertical reticle appearing on the ultrasound imaging monitor/display. The ultrasound operator has the option when to activate this electronic artifact reticle. Various combinations of electronic methods used to send, receive, store, and display the ultrasound information can be designed/programmed to create a narrow column void of imaging information. In one embodiment of the present invention, the ultrasound beam-firing configuration or array scanning pattern and pulse sequences are designed to produce the reticle. Additionally, the signals from one or a combination of several ultrasound transducer elements can electronically be temporarily ignored or blocked to guide/refine the technologist's/ultrasound operator's field of view.

BRIEF DESCRIPTION OF THE DRAWINGS

FIG. 1E shows the device attached to an ultrasound transducer.

DETAILED DESCRIPTION

Figure 1A:
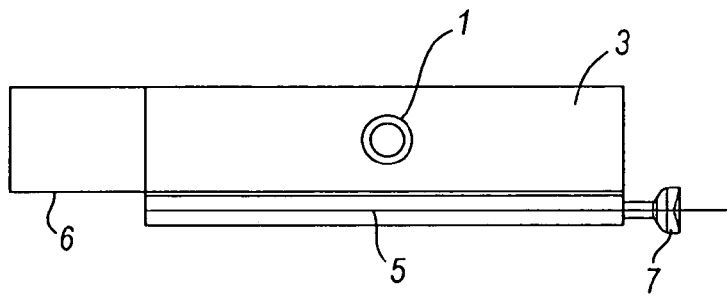
FIGS. 1A–E: Top view (FIG. 1A), isometric view (FIG. 1B), front view (FIG. 1C), and side view (FIG. 1D) of a device according to the invention.
Figure 1C:
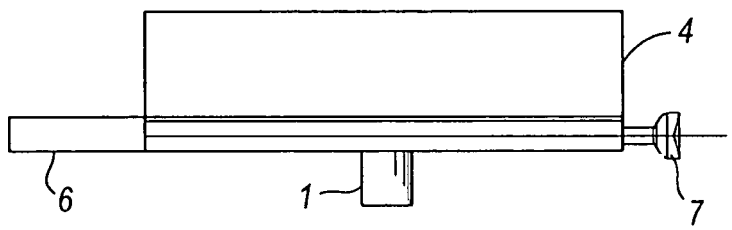
Figure 1D:
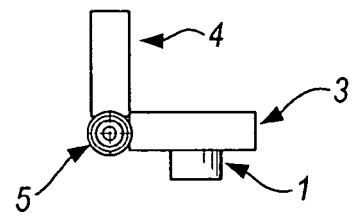
Figure 1B:
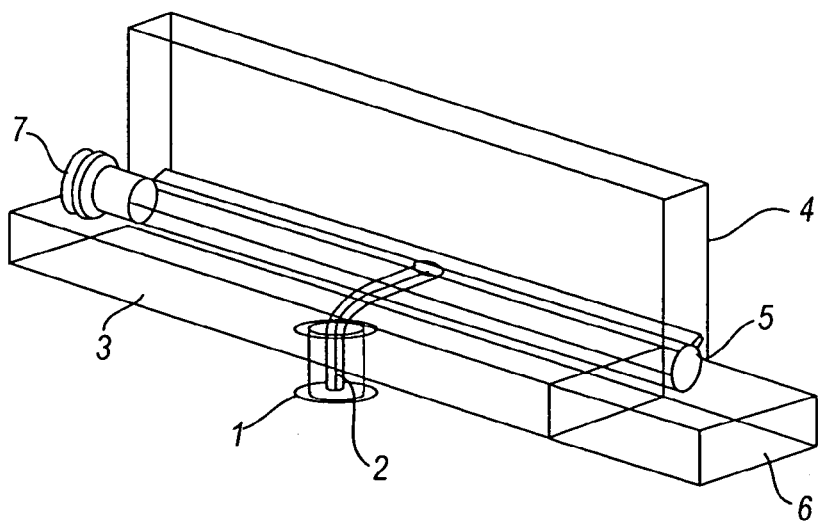
Figure 1E:
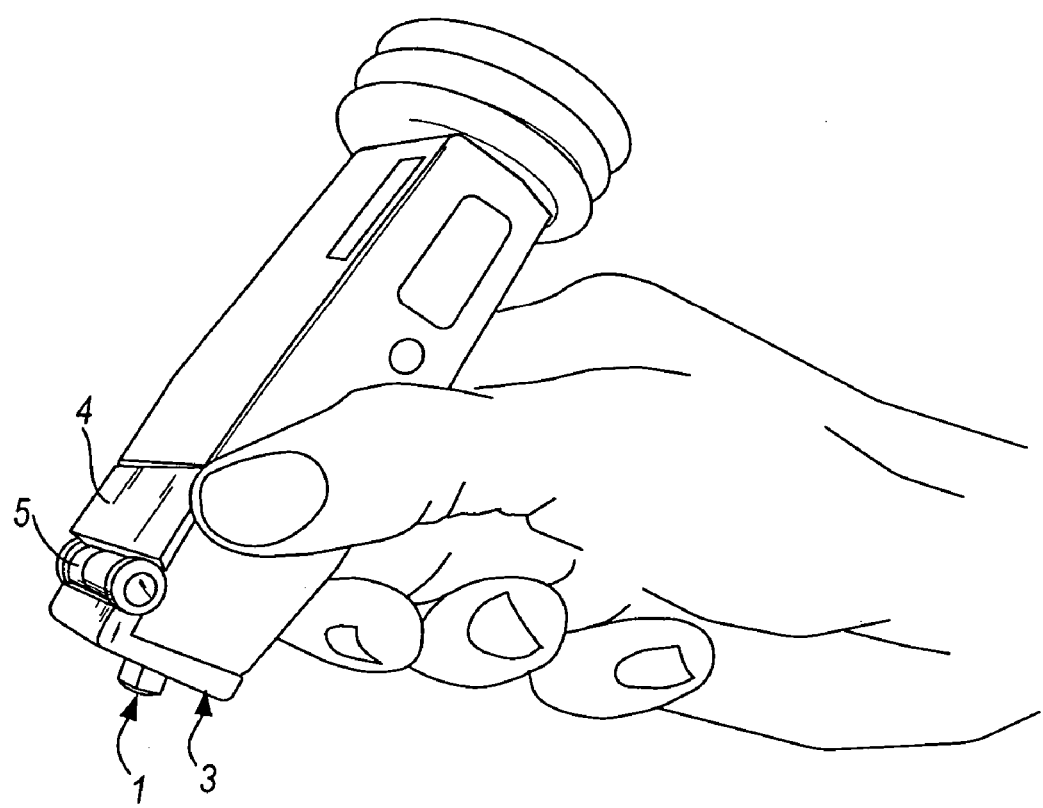

The present invention provides a method and device (e.g., an ultrasound accessory) for marking a patient's skin. In one embodiment, the device comprises a first portion/element and a second portion, with the first portion being rotatably attached to the second portion. In a preferred embodiment of the device, the first portion 4 and second portion 3 of the device are attached to each other by means of a hinge 5 (see FIGS. 1A–E). Other means of rotating the second portion with respect to the first portion can be used instead of a hinge. Such means are well known in the art. For instance, two spherical, spaced-apart protrusions attached to one side of the second portion could be snap-fit into two hollow grooves or indents formed on one side of the first portion.

The first portion is adapted so that the device that can be readily attached to and removed from a diagnostic ultrasound transducer. For instance, the first portion of the device will be sized and shaped to so that it can be attached to the ultrasound transducer (see FIG. 1E).

In addition, the first portion of the device will preferably be equipped with a means for properly aligning and/or attaching the device to the transducer for optimal accuracy. The device is aligned to the ultrasound transducer in a manner which assures that the mark made on the patient's skin by the device, once aligned by the ultrasound operator, will be precisely centered on the ultrasound image which has been produced on the screen by the transducer. For example, a spatial ruler sticker could be incorporated onto the device to facilitate determining the exact center of the transducer during placement of the device.

The first portion of the device is preferably securely attached to the transducer. Any means of removable attachment can be used, including e.g., an adhesive sticker, velcro, snap or slide. In an alternate and preferred embodiment of the invention, attachment elements for the device can be integrated with the ultrasound transducer housing. The ultrasound transducer can be manufactured with a coupling system, which may include a snap or slide connector, lock-joint or matching shape type of coupling on the transducer housing, which matches a counterpart on the marking device. Since the marking device is preferably separable from the transducer, it can be disposed of, or cleaned, after each patient use. Thus, in one embodiment of the present invention a disposable device is contemplated, while in others, a re-usable, preferably sterilizable device is employed.

The second portion of the device is preferably not attached to the transducer and is rotated relative to the first portion so that it is spaced away from the skin of a patient during the ultrasound examination to identify a feature or features of interest. The second portion is equipped with a marker element for marking the skin of the patient. For instance, the marker element may be an element for indenting the skin of the patient and/or an element for marking the skin of a patient with permanent or other suitable ink, paint, crayon, grease, marker, etc. (hereinafter generally referred to as "ink"). When a feature of interest is observed, the second portion is rotated toward the skin of the patient until the marker element comes into contact with and marks the patient's skin.

When the marker element is an element for indenting a patient's skin, it can be made of any material and can be any shape which allows for the making of an indent in the patient's skin. Preferably, the shape of the skin contacting element and the pressure used to apply the same against the skin is selected to provide a marking that is sufficient to be viewed and/or felt (palpated) on the skin by an operator of the device, for a period of at least about 3 seconds, more preferably about 5 seconds, and most preferably more than about 7 seconds. Preferably the pressure and/or shape is not sufficient to penetrate the skin in a manner that will cause bleeding. For instance, it can be a hollow cylinder attached to the second portion of the device (see FIG. 1B), a perpendicularly-centered projection from the surface of the second portion, or the like, permanently attached (e.g., by gluing) to, or integral with, the second portion.

With reference to FIGS. 1A–E, the second portion 3 is preferably spaced away from the skin of the patient during an ultrasound examination to locate a feature of interest.

When a feature of interest is observed, the second portion 3 is rotated about the hinge 5 until the marker (indent) element 1 is in contact with the patient's skin. The second portion can be rotated either manually, or additionally fitted with a finger tab 6 or by depressing a spring-loaded mechanism which rotates the second portion toward the skin of the patient. Depressing the second portion causes the formation of an indent in the patient's skin representing the relative position of the feature of interest. The indent element will leave a slightly reddened and depressed mark which may be any shape, such as a circle, and is preferably no more than 5 mm in its greatest dimension to minimize discomfort for the patient and to provide a precise target for the physician. The indent will remain visible for a period of time at least long enough to complete the ultrasound examination. Once the ultrasound examination is completed and all of the features of interest have been marked with indents, the ultrasound gel can be removed from the skin of the patient, and the indents marked with ink using a permanent marking pen to preserve the marks for a longer period of time, if desired.

In other preferred embodiments, the device is configured so that the patient's skin can be marked with ink or is configured so that the patient's skin can be marked with ink, indents, or both, at the option of the ultrasound operator. To mark a patient's skin with ink, the device may comprise an incorporated ink delivery system. Methods of marking with ink include, but are not limited to, a retractable ink stamp or pre-inked wick type applicator mechanism whereby the opening of the marker element 1 is additionally nested with a retractable ink delivery system 2 or other element of an ink dispensing system (see FIG. 1B). This embodiment further comprises a communication with a hollow hinge 5 and regulator 7, allowing for the supply of an ink from a retractable ink stamp or pre-inked wick-type applicator mechanism through an ink delivery system outlet 2, through the gel, to the skin. The stamp or wick applicator mechanism may be retracted inside the marker element 1 between marking sites to avoid unnecessary marks. Inside the marker element 1, it can be further retracted so that it may be encased in a housing provided by the second portion 3 and hinge 5. A channel may connect the ink delivery system 2 to an ink reservoir through an otherwise hollow hinge 5. The deployment of the stamp or wick applicator mechanism through the channel is controlled by a regulator 7 at the end of the hinge 5 which prevents or allows the stamp or wick applicator mechanism or ink to be deployed through the channel to the ink delivery system 2. An alternate may consist of, but is not limited to, an opening at the distal end of the ink delivery system 2 through which ink, sealed in a liquid-tight state, is introduced through the applicator which is nested inside the marker element 1. The flow of ink through the channel is preferably controlled by a regulator 7 at the end of the hinge 5, which deploys ink through the channel to the ink delivery system outlet 2.

The device of the present invention may be made of any suitable material(s). Preferably, the device is made of a plastic material which is suitable for the manufacture of disposable devices and which is highly permeable to ultrasonic beams and gives rise to minimal reverberation and attenuation of reflected ultrasonic beams.

The device and method of the invention can be used in any ultrasound examination where it is desired to mark features of interest on the skin of the patient (a human patient or non-human animal patient) being examined. The device and method of the invention may also be used in intravaginal ultrasound examinations, as well as in intraoperative ultrasound examinations. Specific types of ultrasound examinations in which the method and device of the invention can be used include:

Venous vascular applications, such as vein mapping prior to harvest, perforator vein marking prior to surgical ligation, lesser saphenous origin prior to surgical ligation or venous valves prior to valvuloplasty or transposition surgery, denoting proximal end of deep venous thromboses to monitor for propagation on follow up studies, denoting thrombus length for investigational purposes to determine propagation patterns for various low molecular weight heparins/also whether prolonged treatment with anticoagulation improves long term lysis, marking subclavian or femoral vein for catheterization procedures, venous malformation prior to percutaneous ablation;

Arterial vascular applications, such as marking the length of occlusion or site of arterial graft stenosis prior to focal surgical revision or prior to insertion of a stent or endostent, marking patent section of target artery prior to bypass surgery which may be poorly visualized on angiography or magnetic resonance angiography, marking fistula prior to focal surgical revision, marking for ultrasound-guided pseudoaneurysm repair by manual compression or thrombin injection and for follow-up scan possibly with re-injection, marking small pseudoaneurysms for surgical repair, mapping radial artery prior to harvest for conduit for cardiac surgery, denoting Vasoseal™ migration, marking carotid bifurcation prior to endartectomy surgery without arteriogram, marking optimal transcranial doppler window;

General ultrasound examinations, such as marking breast lesion prior to needle biopsy, marking breast implant leaks, marking thyroid abnormality prior to needle guided biopsy, other tissue or cyst prior to biopsy, fluid aspiration, marking amniotic pocket prior to amniocentesis, marking a hernia prior to surgical repair, denoting extremity pathology, denoting foreign object, pericardiocentesis, renal pelvis aspiration, possible ultrasound contrast usages; and Veterinary ultrasound, such as initial diagnostic ultrasound, marking for liver aspiration, mass aspiration, cystocytesis, evaluating lung pathology, biopsies, detecting organ or tissue abnormalities, assess size of cysts and tumors.

The device and method of the present invention provide for an easy, fast, efficient and accurate ultrasound examination. For example, using the method and device of the present invention, the examination and marking of the greater saphenous vein can be performed in about 40–50% of the time that it takes to perform the conventional examination and marking procedure. The device is simple and easy to use and is inexpensive to fabricate, making increased accuracy and precision very affordable.

Figure 2:
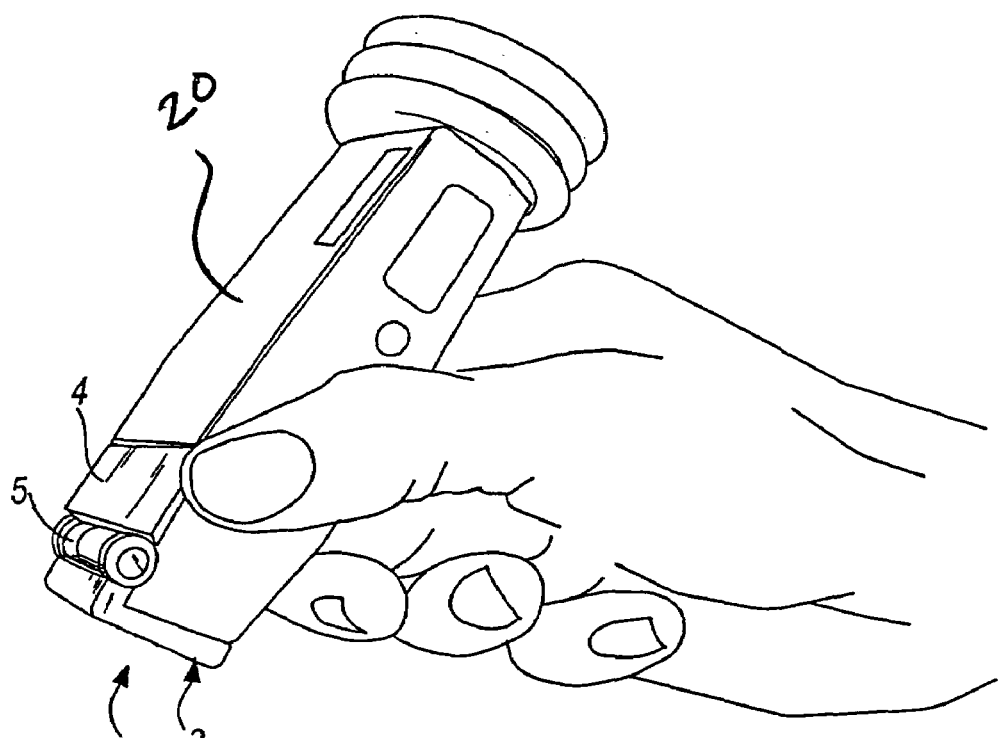
FIG. 2 is a perspective view of an operator/user handling a device in accordance with the present invention.
Figure 3:
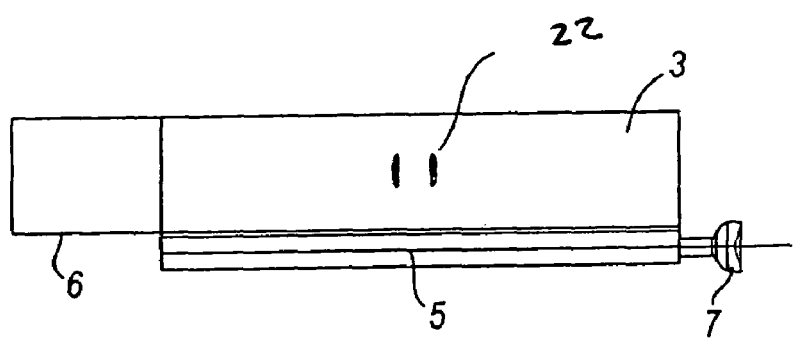
FIG. 3 is a top view of one embodiment of the present invention.

FIG. 2 shows one embodiment of the present invention, which provides a device for guiding an ultrasound transducer 20 during an ultrasound examination. In one embodiment, the device comprises a first element 4 and a second element 3, with the first element being attached for movement to the second element 3. In a preferred embodiment of the device, the first element 4 and second element 3 of the device are operatively associated with each other by means of a hinge 5 or any other suitable adjustable connection feature. The first element 4 is preferably secured to the ultrasound transducer 20. The second element 3 is preferably not permanently fixed or attached to the transducer 20 so that it can be rotated away, or otherwise moved, from the end of the transducer 20 when not in use. As shown in FIG. 3 the second element 3 is equipped with two segments of ultrasound wave interference material 22. The second element 3 may be equipped with or employ various different shapes and sizes of interference material to achieve the desired result (e.g. crosshair shape, circular shape, square outline, thick lines, thin lines, etc.) of effective guidance of the transducer during an examination.

In certain embodiments, ultrasound wave interference material can be integrated within the transmitting end of the ultrasound transducer 20.

While various embodiments of the present invention have been described in detail, it will be apparent that further modifications and adaptations of the invention will occur to those skilled in the art. It is to be expressly understood that such modifications and adaptations are within the spirit and scope of the present invention.

What is claimed is:

1. The method of guiding an ultrasound transducer comprising:
   (a) locating a feature of interest by conducting an ultrasound examination of a patient using an ultrasound transducer, said ultrasound transducer comprising an ultrasound permeable ultrasound accessory having a first element adapted for movement to a second element, said second element having a surface adapted to contact said patient, wherein said second element surface is comprised of an ultrasound permeable material and a portion of ultrasound impermeable material smaller than said second element surface, said portion of ultrasound impermeable material being located substantially in the center of said second element surface so that it generates a negative image reticle on a video monitor/display;
   (b) moving said second element of said ultrasound accessory to contact a patient's skin; and
   (c) relying upon said negative image reticle to guide a user of said ultrasound transducer to locate features of interest.

2. The method of claim 1, wherein said portion of ultrasound impermeable material has a first segment of ultrasound impermeable material a fixed distance from a second segment of ultrasound impermeable material.

3. An ultrasound accessory for marking a patient's skin comprising:
   (a) a first element adapted to be attached to an ultrasound transducer;
   (b) a second element adapted for movement with respect to said first element, said second element contacting a surface subject to ultrasound examination, wherein at least one of said first element and said second element are comprised of an ultrasound permeable material, and wherein at least one of said first element and said second element are movably associated with each other, said second element having at least a portion comprising substantially ultrasound impermeable material that facilitates the generation of a visual feature on an ultrasound image;
   (c) a marking element capable of marking a patient's skin with ink, paint, crayon or grease, said marking element attached to said second element, said marking element comprising a substantially perpendicularly-centered projection on said second element of said ultrasound accessory; and
   (d) a means for aligning said ultrasound accessory to assure a mark made by said marking element corresponds to an ultrasound image produced by said transducer.

* * * * *